(12) United States Patent
Treiman

(10) Patent No.: US 7,163,617 B2
(45) Date of Patent: Jan. 16, 2007

(54) CHEMICAL PROPORTIONING AND DISPENSING SYSTEMS

(75) Inventor: Michael T. Treiman, Los Angeles, CA (US)

(73) Assignee: Platinum Technologies Company, LLC, Beverly Hills, CA (US)

( * ) Notice: Subject to any disclaimer, the term of this patent is extended or adjusted under 35 U.S.C. 154(b) by 84 days.

(21) Appl. No.: 10/687,847

(22) Filed: Oct. 17, 2003

(65) Prior Publication Data

US 2005/0084414 A1    Apr. 21, 2005

(51) Int. Cl.
F17D 1/08 (2006.01)

(52) U.S. Cl. ............... 210/101; 210/137; 137/1; 422/28; 422/36; 422/256

(58) Field of Classification Search ............... 422/3, 422/28, 36, 256, 257; 137/1, 565; 220/647, 220/101, 137; 210/101, 137, 647
See application file for complete search history.

(56) References Cited

U.S. PATENT DOCUMENTS

| | | | |
|---|---|---|---|
| 1,105,581 A | 7/1914 | Rusby | |
| 2,719,704 A | 10/1955 | Anderson et al. | |
| 3,756,457 A | 9/1973 | Holmes et al. | |
| 4,781,467 A | 11/1988 | Williams | |
| 5,159,958 A | 11/1992 | Sand | |
| 5,230,368 A | 7/1993 | Berfield | |
| 5,253,677 A | 10/1993 | Sand | |
| 5,351,875 A | 10/1994 | Rhine et al. | |
| 5,424,323 A | 6/1995 | Wachman et al. | |
| 5,439,020 A | 8/1995 | Lockhart | |
| 5,522,419 A | 6/1996 | Sand | |
| 5,597,544 A | 1/1997 | Barber et al. | |
| 5,653,261 A | 8/1997 | Dalhart et al. | |
| 5,678,593 A | 10/1997 | Lockhart | |
| 5,743,637 A | 4/1998 | Ogier | |
| 5,799,831 A | 9/1998 | Spriggs et al. | |
| 5,927,338 A | 7/1999 | Boticki et al. | |
| 6,079,595 A | 6/2000 | Meyer et al. | |
| 6,095,675 A | 8/2000 | Tai | |
| 6,098,651 A | 8/2000 | Boticki et al. | |
| 6,293,153 B1 * | 9/2001 | Grune et al. ............... 73/714 |
| 6,299,035 B1 | 10/2001 | Dalhart | |
| 6,619,318 B1 * | 9/2003 | Dalhart et al. ......... 137/565.34 |
| 6,655,401 B1 * | 12/2003 | Sand et al. ................. 137/1 |
| 2002/0061263 A1 * | 5/2002 | Taylor ................... 422/129 |
| 2002/0061474 A1 * | 5/2002 | Buongiorne et al. ...... 430/434 |
| 2003/0150936 A1 * | 8/2003 | Bristor ................... 239/307 |
| 2004/0037737 A1 * | 2/2004 | Marais et al. ............. 422/28 |
| 2004/0156744 A9 * | 8/2004 | Stanley .................. 422/28 |

* cited by examiner

Primary Examiner—Krisanne Jastrzab
Assistant Examiner—Sean E. Conley
(74) Attorney, Agent, or Firm—Christie, Parker & Hale, LLP

(57) ABSTRACT

Chemical proportioning and dispensing systems discussed herein include systems for producing a desired admixture ratio of a first fluid and one or more other fluids. The systems may include one, two, or three eductors with each eductor including one or two suction inlet ports. An admixture of one or more than one fluids may be outputted via a common output header or from a single eductor outlet port having two suction inlet ports. The admixture may be used to sterilize or disinfect a number of equipment and surfaces including those found in a health care facility. Finally, the ratio of admixture may be adjusted by controlling the pressure drop of the suction inlets and/or the supply pressure of the motive source. Methods for utilizing the chemical proportioning and dispensing systems are also discussed.

3 Claims, 4 Drawing Sheets

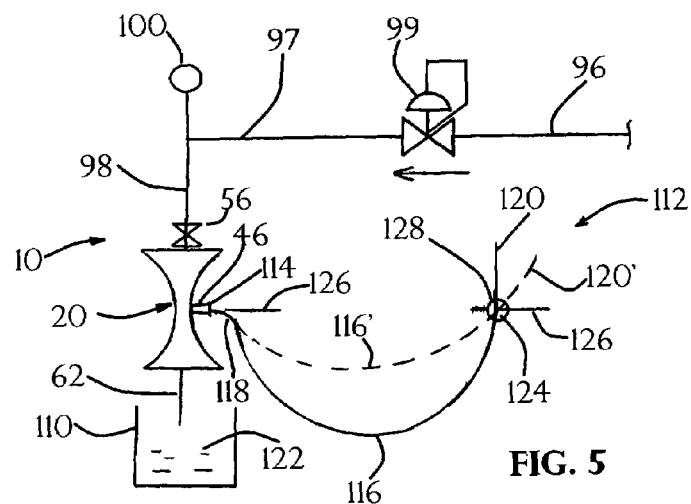
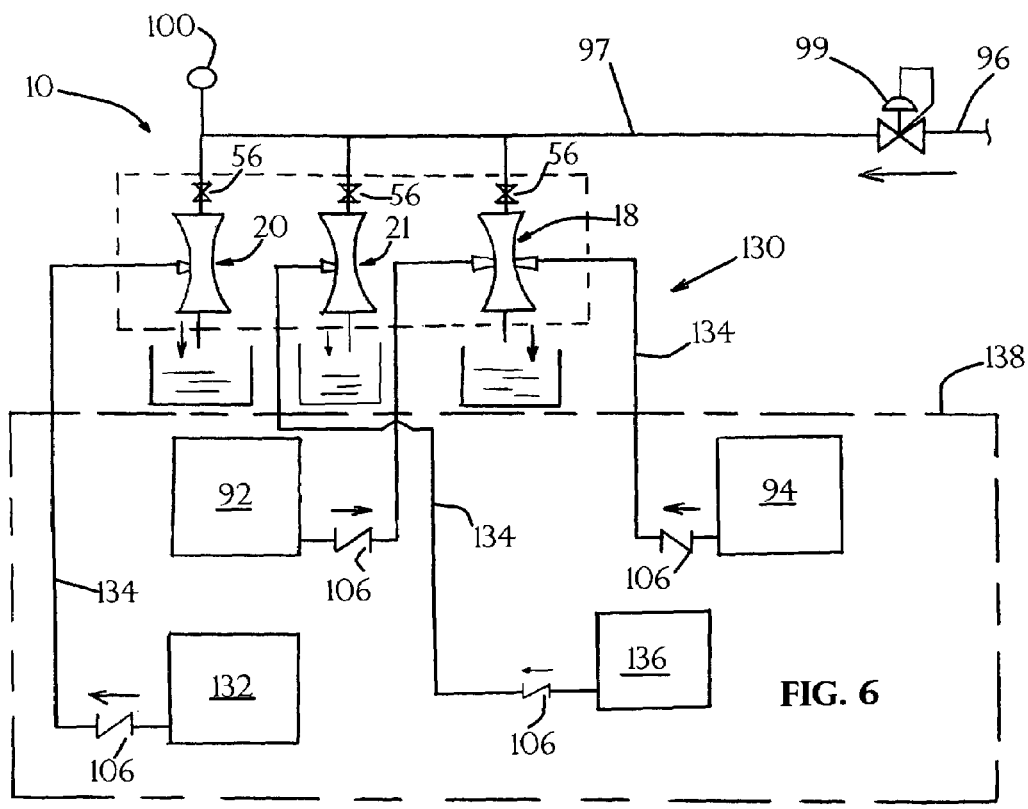

CHEMICAL PROPORTIONING AND DISPENSING SYSTEMS

Chemical proportioning and dispensing systems discussed herein include systems for automatically producing a desired admixture ratio of a first fluid and one or more other fluids.

BACKGROUND

Sterilants are germicides that kill all microorganisms and are widely used in the prior art for sterilization, hygiene purposes, as a disinfectant, and other related purposes. Sterilants are typically commercially available in a ready-to-use form or in a concentrate to be diluted into an admixture on-site.

In the ready-to-use form, sterilants generally comprise 2–15% by weight or volume of active ingredients and a balance of water. Due to the high water concentration, it is generally not efficient to ship ready-to-use sterilants as the bulk of the shipment is water. Hence, from the perspective of an end user, purchasing ready-to-use sterilants are generally not as cost effective.

In the concentrated form, sterilants are typically available in bulk packages, such as a 1-gallon bulk, 5-gallon bulk, and a 55-gallon drum, etc. Sterilants are also available in two or more concentrated solutions to be blended on-site. A sterilant can comprise a container of diluent or pH adjusting agent and a separate container of aliphatic dial, such as a dialdehyde, for on-site mixing with water to form an admixture of ready-to-use sterilant.

When a concentrated sterilant is acquired for use, a user must first dilute the concentrate into a final acceptable ratio/admixture. The mixing process may be accomplished by dispensing the concentrated sterilant in a suitable container and diluting it with water and/or other solutions, such as diluents or pH adjusting agents, to achieve the correct concentration. As can be expected, this manual method of mixing can occasionally lead to mixing errors and can unnecessarily expose the user to concentrated chemicals.

Accordingly, there is a need for a dispensing and proportioning system for mixing concentrated chemicals that is accurate, dependable, effective and that minimizes direct user contact with concentrated chemicals.

SUMMARY OF THE PREFERRED EMBODIMENTS

According to the present invention, there is provided a method for diluting a concentrated solution of sterilant for sterilizing instruments or equipment comprising the steps: providing an eductor, the eductor comprising a metering tip having a first orifice size, a chemical inlet port, and a water inlet port; hooking a container containing concentrated sterilant to the chemical inlet port of the eductor; hooking a water supply source to the water inlet port of the eductor, the water supply source comprising a regulating valve for regulating a working pressure of the water supply; activating the eductor to mix water and concentrated sterilant to a desired admixture containing a volume of sterilant to a volume of water; adjusting the admixture by varying the volume of the sterilant to the volume of water by varying at least one of the metering tip to one having a second orifice size or the working pressure of the water supply to the eductor; and using the admixture to sterilize an instrument for use in treating a subject.

According to another practice of the present invention, there is provided a method for diluting a concentrated chemical solution with water for use in a health care facility comprising the steps: providing an eductor housed in a housing; adjusting the eductor's output by adjusting a regulated valve to adjust a water supply pressure to a first pressure and adjusting a chemical inlet back pressure by selecting a metering tip having a first orifice size; hooking an inlet line connected to a container containing the concentrated chemical solution to the eductor's chemical inlet port; hooking an inlet line from a water supply source downstream of the regulating valve to the eductor's water inlet port; activating the eductor so that water flows through the water inlet port and concentrated chemical solution flows through the chemical inlet port; outputting the admixture into a holding container; and applying the admixture to a surface inside a health care facility.

According to another practice of the present invention, there is provided an apparatus for diluting a concentrate comprising: a proportioning and dispensing unit comprising at least two eductors, wherein a first eductor comprises a first chemical inlet port, a second chemical inlet port, a motive source inlet port, and an outlet port; a first container containing a concentrate having a container outlet port and a first hose connecting the container outlet port to the first chemical inlet port; a second container containing a pH adjusting agent having a container outlet port and a second hose connecting the container outlet port to the second chemical inlet port; a line connecting a motive source to the motive source inlet port, the line comprising a regulating valve for regulating pressure supplied by the motive source, a third hose for connecting to the outlet port of the eductor; a push button for opening a valve on the first eductor so as to permit motive source to flow through the first eductor; and wherein a first metering tip is removably received in the first chemical inlet port and a second metering tip is removably received in the second chemical inlet port.

In accordance to still yet another practice of the present invention, there is provided a method for dispensing an admixture of fluid and water in a proportioning and dispensing unit comprising the steps: (a) selecting a first metering tip comprising a first orifice size and coupling the metering tip to a chemical inlet port of an eductor, said eductor further comprising a water inlet port and an outlet port; (b) connecting the water inlet port to a water supply source, said water supply source comprising a pressure regulator having a first water pressure set point; (c) placing a holding container at the outlet port of the eductor for receiving an output stream from the eductor; (d) selecting a first hose comprising a hose length, a first end, a second end, and unit gradations along at least a portion of the hose length; (e) placing the first end of the first hose in fluid communication with the metering tip; (f) filling the hose length with a quantity of fluid to a starting fluid level; (g) activating the eductor to produce the admixture of fluid and water at the outlet port; (h) de-activating the eductor to stop producing the admixture at the outlet port; (i) determining an amount of fluid solution dispensed from the eductor by measuring the unit gradations on the first hose between the starting fluid level and a second fluid level measured after the eductor is de-activated; (j) determining a percent ratio of fluid dispensed to water used to dispense the fluid through the eductor; and (k) if the percent ratio of fluid to water is not as desired, changing at least one of the first metering tip having the first orifice size to a second metering tip having a second orifice size or the first water pressure set point of the pressure regulator to a second water pressure set point, and repeating steps (f) to (j).

Yet according to another practice of the present invention, there is provided a method for dispensing an admixture of concentrated chemical solution and water in a proportioning and dispensing unit comprising: mounting two eductors to a housing and mounting the housing in a health care facility, the two eductors having a common water inlet header; connecting a first chemical to a chemical inlet port of the first eductor; connecting a second chemical to a chemical inlet port of the second eductor; connecting a water supply line to the common water inlet header; the water supply line comprising a regulating valve; activating at least one of the first eductor or the second eductor to produce an admixture of at least one of the first chemical and water or the second chemical and water; and wherein the chemical inlets of the first and second eductors each comprises a metering tip having an orifice.

Other alternatives and embodiments for practicing the invention are also described herein and further discussed below in the Detailed Description section.

BRIEF DESCRIPTION OF THE DRAWINGS

These and other features and advantages of the present invention will become appreciated as the same become better understood with reference to the specification, claims and appended drawings wherein:

FIG. 5 is an exemplary block flow diagram of a proportioning and dispensing system comprising the proportioning and dispensing assembly of FIG. 1 in a calibration service;

FIG. 6 is an exemplary block flow diagram of a proportioning and dispensing system comprising the proportioning and dispensing assembly of FIG. 1 in service with three fluids to be dispensed and proportioned.

DETAILED DESCRIPTION OF THE PREFERRED EMBODIMENTS

The detailed description set forth below in connection with the appended drawings is intended as a description of the presently preferred embodiments of the dispensing an proportioning system provided in accordance with practice of the present invention and is not intended to represent the only forms in which the present invention may be constructed or utilized. The description sets forth the features and the steps for constructing and using the dispensing and proportioning system of the present invention in connection with the illustrated embodiments. It is to be understood, however, that the same or equivalent functions and structures may be accomplished by different embodiments that are also intended to be encompassed within the spirit and scope of the invention. Also, as denoted elsewhere herein, like element numbers are intended to indicate like or similar elements or features.

Figure 1:
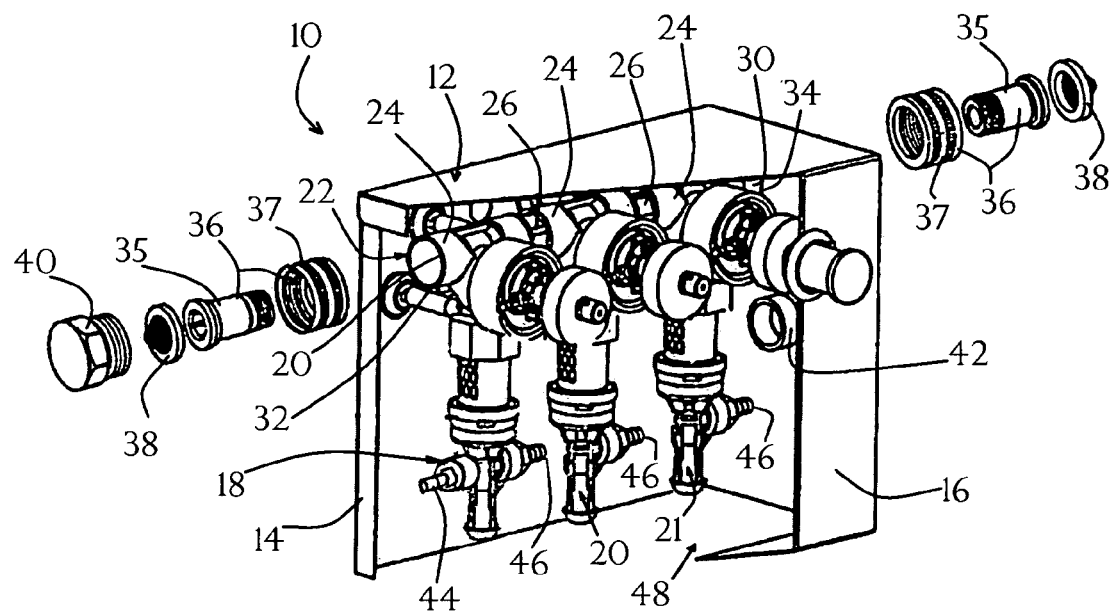
FIG. 1 depicts a semi-schematic partial exploded perspective view of a proportioning and dispensing assembly comprising three eductors provided in accordance to one practice of the present invention.

Referring now to FIG. 1, there is shown a semi-schematic partial exploded perspective view of a proportioning and dispensing assembly (herein "assembly") provided in accordance with aspects of the present invention, which is generally designated 10. The assembly 10 comprises a housing 12, which includes a back housing panel 14, and a front housing panel 16. Mounted to the housing 12, and particularly to the back housing panel 14, is a plurality of eductors 18, 20, 21 each extending from a common inlet header 22.

The common inlet header 22 is configured to pass a motive source, such as water, and generally comprises the upper portions of the eductors 18, 20, 21, which are the valve bodies 24, connected end-to-end by pipe nipples 26. At the two ends 28, 30 of the header 22, i.e., at the valve body end 28 of eductor 18 and the valve body end 30 of eductor 21, are female threaded couplings 32, 34. The female threaded couplings 32, 34 are configured to connect to motive supply sources, such as a water line, to supply the necessary motive force for the eductors 18, 20, 21. In one embodiment, the two threaded couplings 32, 34 on the two ends of the header 22 are fitted with conventional swivel connectors 36, which comprise a swivel stem 35 and a swivel collar 37. Although two motive sources may be used with the assembly 10 shown, only one motive supply source is utilized. Accordingly, the valve body end 30 of the right eductor 21 is fitted with a strainer 38 for straining the incoming supply and the valve body end 28 of the left eductor 18 is fitted with a plug 40.

The housing 12 also includes a bushing 42 for access purposes to the interior of the housing from the exterior of the housing. For manipulating the three eductors 18, 20, 21, such as connecting to the suction inlets 44, 46 of the three eductors, the housing further includes a bottom access opening 48. The bottom access opening 48 is approximately the size of the entire lower surface of the housing 12 to provide ample clearance for the various connections to the assembly 10. The front panel 16 also separates from the back panel 14 to provide access to the eductors 18, 20, 21.

The assembly 10 shown in FIG. 1 is commercially available from Hydro Systems Company of Cincinnati, OH, and at the website http://www.hydrosystemsco.com. The assembly 10 is available under the trade name AccuDose Series Proportioner with E-Gap Eductor in a 1, 2, or 3 button unit, which corresponds to a unit having 1, 2, or 3 eductors. The assembly 10 shown is a 3 button unit. However, a 2 or a 1 button unit may be used interchangeably with the 3 button unit depending on the number of eductors required for the particular application. The eductors are available in a single suction inlet 46 model, such as eductors 20 and 21, or in a dual suction inlet 44, 46 model, such as eductor 18. In use, the assembly 10 can be mounted on a wall, near a sink, in a closet space, in a cabinet, or near the general vicinity of a motive source and the fluid or fluids to be mixed.

Figure 2:
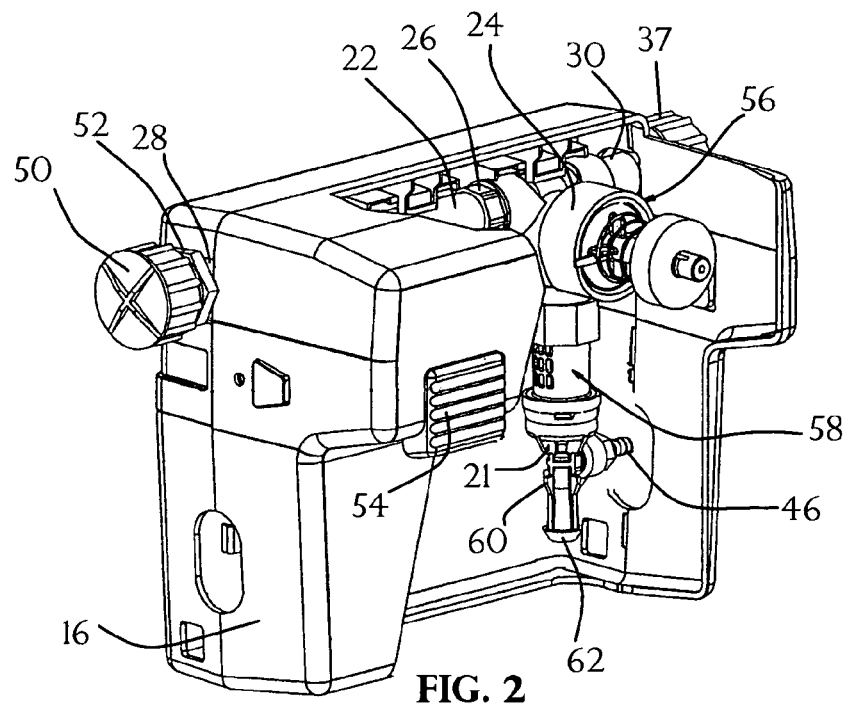
FIG. 2 depicts a semi-schematic perspective view of the proportioning and dispensing assembly of FIG. 1 with a partial view of the cover comprising an activation button.

Referring now to FIG. 2, there is shown a semi-schematic perspective view of the assembly 10 of FIG. 1 with modifications to the header 22. As shown, a connector fitting cap 50 is attached to a connector fitting 52, which is then connected to the swivel collar 37 of the left valve body end 28. Also shown in FIG. 2 is a push button 54 for activating the eductor valve 56 situated subjacent the push button.

The assembly 10 works as follows: when the push button 54 is depressed, the eductor valve 56 opens up to allow the motive source, such as water, to enter the header 22 via the right valve body end 30. The motive source then enters the valve body 24 and travels through to the eductor body housing 58 then on through to the reduced section 60 of the eductor. As the motive source travels pass the reduced section 60, its velocity increases, which creates a low-pressure region as explained by Bernoulli's principle. The motive source then exits the eductor outlet 62 to a waiting collection container (not shown). Because fluids travel from a high-pressure region to a low-pressure region, fluid (not shown) connected to the suction inlet 46 flows through the suction inlet and exits the outlet 62 along with the motive source. In short, the assembly 10 shown enables a user to mix a concentrated fluid with a motive source to form an admixture of the concentrated fluid to motive source, i.e., a dilution. The assembly 10 also permits the user to regulate the flow of the fluid and the motive source to vary the ratio or percent makeup of the two by changing a metering size and/or changing the pressure of the motive source, as further discussed below.

Figure 3:
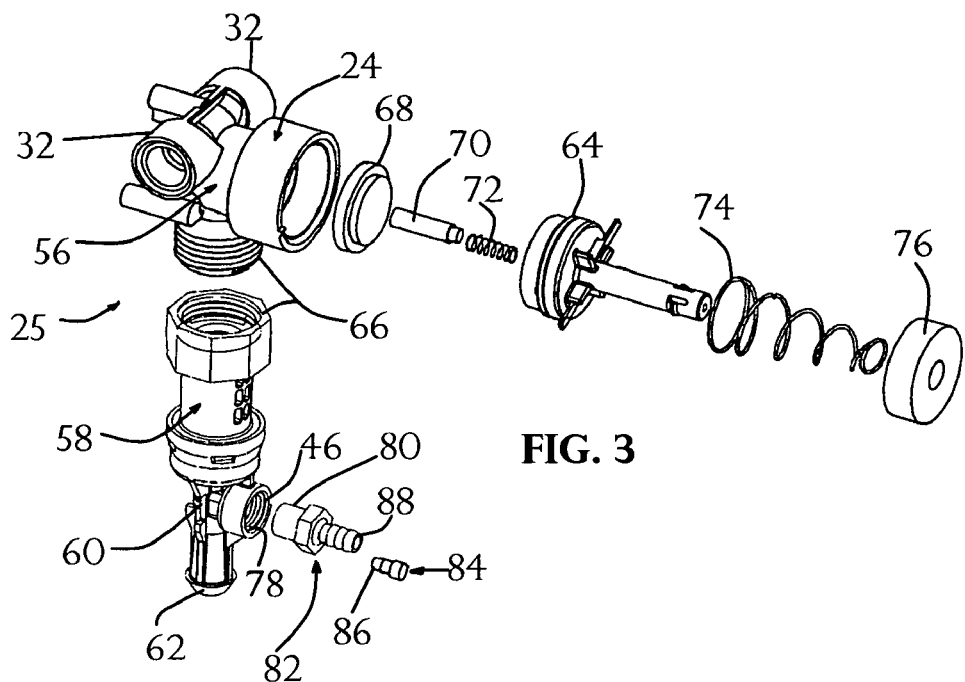
FIG. 3 depicts a semi-schematic exploded perspective view of one of the eductors of FIG. 1.

Referring now to FIG. 3, there is shown an exploded perspective view of one of the eductors 20 of FIG. 1. The eductor 20 shown is a single suction inlet eductor, which is essentially the same as the dual suction inlet eductor 18 except it has one less suction inlet. Broadly speaking, the eductor 20 comprises a valve 25, which includes a valve body 24, a valve bonnet 64, and an eductor housing 58, which includes a reduced section 60, an inlet 46, and an outlet 62. The eductor housing 58 is attached to the valve body 24 via a threaded fitting 66. As readily understood by a person of ordinary skill in the art, the valve 56 is responsible for opening and closing the flow path of the motive source and the eductor housing 58 is responsible for regulating, at least in part, the amount of fluid that enters the eductor inlet 46. Other valve components incorporated in the eductor 20 include a diaphragm 68, an armature 70, a spring 72, a second spring 74, and a magnet 76. The function and operation of these various components, including the entire eductor 20, are well known and are incorporated in the commercial embodiment of the AccuDose system offered by Hydro Systems Company. Further discussion is not believed necessary.

Referring again to the eductor housing 58 and particularly to the inlet 46 of the eductor 21, there is shown a female threaded receptacle 78 for receiving a male end 80 of a hose barb assembly 82. The hose barb assembly 82 is, in turn, configured to receive a metering tip 84, which has an orifice therein for regulating the amount of flow that flows therethrough. The metering tip 84 is connected to the barb assembly 82 by pushing the male end 86 of the metering tip into the opening 88 of the barb assembly, which then couples the two in a slight interference fit. The metering tip 84 is available from Hydro Systems Company in a variety of orifice sizes ranging from 0.006" (having Hydro part No. 10027004) to 0.128" (having Hydro part No 690012). The metering tip is also available with a closed end so that a custom orifice size may be drilled therethrough for a custom configuration.

Although not shown, the eductor 20 may be equipped with a discharge tube connected to the outlet 62 having sufficient length to extend into a bucket or a container to minimize splattering at the outlet. On the inside of the eductor housing 58, the eductor 20 may be equipped with a back-flow prevention device (not shown). The back-flow prevention device can prevent back-flow of the fluid to be blended into the motive supply line by sealing off the fluid path of the motive supply line. Further discussion of the back-flow prevention device is not believed necessary as the same is available from Hydro Systems Company and its operation is well known.

Figure 4:
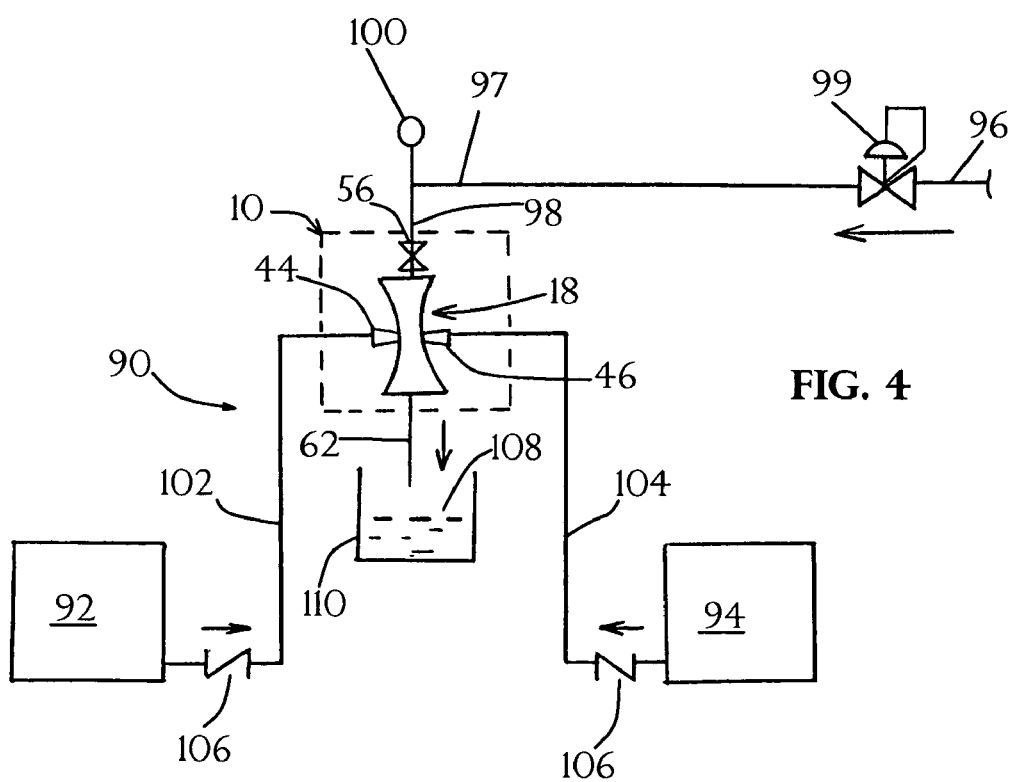
FIG. 4 is an exemplary block flow diagram of a proportioning and dispensing system comprising the proportioning and dispensing assembly of FIG. 1 in service with a motive supply line, a pressure regulator, and two fluids to be dispensed and proportioned.

Referring now to FIG. 4, there is shown a block flow diagram of a proportioning and dispensing system 90 (herein "system") provided in accordance with aspects of the present invention, which comprises the assembly 10 of FIG. 1 in use with two fluid sources 92, 94, and with one eductor 18. Broadly speaking, the system 90 shown is configured to automatically produce a desired admixture ratio of diluted sterilant at the outlet 62 of the eductor 18 with the push of a button 54 (FIG. 2) and with minimum user intervention. As used herein, the term sterilant includes a disinfectant, an antiseptic, a sporicide, a virucide, and a fungicide.

The system 90 may be implemented by connecting a motive source 96, via a pipe or a hose 97, to the motive source inlet 98. Exemplary motive sources include a water supply source, an air supply source, an inert gas supply source, or similar sources that have sufficient pressure for generating a Bernoulli effect at the reduced section of the eductor. The motive source should also be compatible with the fluid to be mixed or blended. The line for the motive source 96 may also include a pressure regulating valve 99 and a pressure gauge 100. Exemplary pressure regulating valves include valves available from McMaster-Carr having an outlet pressure rating in the range of about 2–125 psi and a maximum inlet pressure rating of about 75 psi to about 400 psi. Standard pipe or tube fittings and adapters may be necessary to complete the various connections. Also, plastic tubing and metal piping may be used provided they are rated for such service.

Fluid sources useable with the system 90 of the present invention include a container of diluent 92, such as a pH adjusting agent, and a container of concentrated glutaraldehyde 94. Water is preferably used as the motive source with the diluent and the glutaraldehyde. The diluent, the glutaraldehyde, and water, when blended or mixed, produces an effective sterilant for sterilizing equipment, working surfaces, and the like. Both the diluent and the glutaraldehyde are available from Cetylite Industries, Inc. of Pennsauken, N.J. and at the following web site: http://www.cetylite.com/, under the trade name Cetylcide-G. The specific disclosure of the sterilant is described in U.S. Pat. No. 5,424,323, the content of which is expressly incorporated herein by reference. In one embodiment, the sterilant is a 50% by weight solution of glutaraldehyde concentrate to water. The diluent is a mixture of alkyl benzyldimethylammonium chloride, cetyldimethylammonium bromide, isopropyl alcohol, propylene glycol, sodium nitrite, EDTA, and water, which is more fully disclosed in the '323 patent. In one embodiment, the admixture produceable by the proportioning and dispensing system 90 is a sterilant disclosed in Example B, Col. 11, lines 35–41, of the '323 patent. In another embodiment, the admixture produceable by the system 90 is disclosed in Example A, Col. 10, line 64 to Col. 11, line 5 of the '323 patent. Other embodiments include a system capable of producing variations of the components disclosed in Examples A and B and throughout the '323 patent disclosure by varying the metering size and/or the pressure of the motive source.

By way of examples, other concentrates useable with the proportioning and dispensing assembly of the present invention include Tri-Cide disinfectant cleaner and Ultrasonic solution both from Health Sonics Corp. of Livermore, Calif. The Tri-Cide disinfectant has a dilution ratio of 256:1 while the Ultrasonic solution is available in a 40:1 and a 80:1 blend. By no means limited to the particular examples described, still other concentrates useable with the apparatus of the present invention include Disinfectant Cleaner, Lemon odor #V900, having a dilution ratio of 64:1, Code Blue Iodine Disinfectant having a dilution ratio of 1 oz. per 5 gallon water, Pine Oil Disinfectant having a dilution ratio of 1 oz. per gallon of water, and Dual-27 Quaternary Disinfectant having a dilution ratio of 2 oz. per gallon of water, all available from Biochem Corp. of Coral Springs, Fla. Another concentrate includes concentrated photochemical, such as the Flat Concentrate Developer/Fixer manufactured by Kodak having a dilution ratio of 1-part concentrate to 2-part water. These concentrates may be diluted in the manner and fashion as discussed below with reference to the concentrated glutaraldehyde.

Referring again to FIG. 4, to produce an admixture at the outlet 62 of the eductor, the diluent 92 is connected, via a tubing line 102, to one suction inlet 44 of the eductor 18 and the concentrated glutaraldehyde 94 is connected, via a second tubing line 104, to the other suction inlet 46 of the eductor 18. For an exemplary admixture comprising 3.2% by weight of glutaraldehyde within ±5% variation, 0.925% by weight of diluent within ±5% variation, and a balance by weight of water, the suction inlet 44 for the diluent 92 is equipped with a metering tip having a 0.022" orifice and the suction inlet 46 for the glutaraldehyde 94 is equipped with a metering tip having a 0.033" orifice. A check valve 106 may be used with each of the tubing lines 102, 104 to eliminate back-flow of mixed fluids from the eductor 18 back into the respective containers. Check valves useable with the system of the present invention are available from Hydro Systems and include check valve part number 10089401. The motive source 96 is ordinary tap water, which has a typical line pressure of about 40–70 psi. In one exemplary embodiment, the water pressure is regulated down to about 15 to about 19 psi, with 17 psi being preferred, by adjusting the regulating valve 99. The tubing 102 size for the diluent 92 is a ¼ inch ID plastic tubing having a length of about 77" measured from the container 92 outlet to the suction inlet 44. The tubing 104 for the glutaraldehyde 94 is similar in length and similar in ID.

When the push button 54 on the front cover 16 of the housing 12 (See, e.g., FIG. 2) is depressed, the valve 56 on the eductor 18 is opened and, in due course, the system 90 produces a desired admixture ratio of diluted steralint 108 to water at the outlet 62, which is 3.2% by weight of glutaraldehyde within ±5%, 0.925% by weight of diluent within ±5%, and a balance of water. A holding container 110, such as a bucket, a beaker, or other storage containers having unit gradations or unit markings, may be used to collect the mixed solution at the outlet 62 of the eductor 18. Subsequent to mixing a desired volume of admixture 108 in the container 110, the system 90 may be stopped by depressing the push button 54 to shut off the valve 56. The admixture 108 can then be used to sterilize dental equipment, medical equipment, working surfaces, furnishing, etc. in a medical facility, such as a medical office, a dental office, a veterinarian office, etc. Once the admixture 108 is prepared, it can be reused continuously for several days or as recommended by the manufacturer as both a disinfectant and a sterilant. At the end of that period, any unused admixture may be safely disposed off as recommended by the manufacturer or as permitted by regulations. When a different admixture ratio is desired, different metering tips having different orifice sizes calibrated in accordance with the methods described below may be used.

Referring now to FIG. 5, there is shown an alternative proportioning and dispensing system 112 provided in accordance with aspects of the present invention. The present system 112 may be incorporated for sizing or calibrating a metering tip 114 for use to produce a desired admixture at the outlet 62 of the eductor 20.

Similar to the earlier system 90, in the present system 112, a motive source 96 is connected to the inlet 98 of the eductor 20 via a piping or tubing line 97 with a regulating valve 99 and a pressure gauge 100 connected therebetween. However, unlike the earlier system 90, the suction inlet 46 is not connected to a fluid container. Instead, a length of flexible tubing 116 having a first end 118 connected to the metering tip 114 and a free second end 120 is used. The flexible tubing 116 may be a vinyl tubing having an ID of about ¼ inch and a length of any dimensions greater than about 6 inches. The flexible tubing 116 preferably comprises unit gradations or markings for indicating the volume of fluid contained in the tubing, such as 1 ml increments. The markings also allow the user to compute the amount of fluid dispensed from the tubing when a starting point and an ending point are known.

To determine or calibrate a metering tip 114 having a desired orifice size for automatically producing a desired admixture 122 at the outlet of an eductor, a first metering tip is selected with some arbitrary starting orifice size, which, for purposes of the following discussion, is 0.025". The regulating valve 99 is then set to about 15 to about 19 psi output pressure with 17 psi being more preferred. The metering tip 114 is then inserted into the barb assembly (FIG. 3) and the tubing 116 connected to the end thereof. The tubing 116 is then filled to a starting mark or gradation level 124 with a fluid to be sampled/mixed. The starting mark 124 is then held to a working level 126 that is approximately at the same elevation as the suction inlet 46. To facilitate such a task, an optional support ring 128, such as an eye-bolt, a hook-bolt or a clamp, may be used to support the second end 120 of the tubing 116. If no support ring 128 is used, the user can simply hold the second end 120.

The eductor 20 is then activated by depressing the push button 54 (FIG. 2) on the front panel 16 of the housing 12 (FIG. 2). Upon activating the eductor 20, a test admixture 122 is produced in the holding container 110. As the eductor is operating, the fluid in the tubing is educted from the tubing 116 and the level inside the tubing begins to drop. To compensate for the changing fluid level in the tubing, the second end 120 of the tubing is raised to keep the fluid level inside the tubing approximately level with the elevation level of the suction inlet 46. This is represented by tubing 116', having a second end 120'. This procedure normalizes the tubing 116 so that a suction lift (when the fluid level falls below the suction inlet) or a suction head (when the fluid level is above the suction inlet) may be avoided at the suction during calibration.

After a short period and after a sufficient quantity of admixture 122 is produced in the holding container 110, the valve 56 is de-activated to stop the motive source 96. An amount of fluid dispensed from the tubing 116 is then recorded by subtracting the unit gradation at the starting point from the ending point. The total amount of admixture 122 is then recorded by measuring the admixture volume in the holding container 110. The ratio by weight of fluid to water, assuming that the motive source is water, is simply the volume of fluid dispensed from the tubing over the total admixture 122 less the fluid volume dispensed from the tube. Expressed in mathematical form, the ratio is computed as follows:

Admixture Ratio=volume of fluid dispensed/(total volume of test admixture−volume of fluid dispensed)  (1)

If the ratio is instead computed in percent by weight, the same equation (1) may be used by multiplying the volume with the density of the fluid and with the density of water. Should the ratio of fluid to water be lower than desired, the same procedure may be repeated using a metering tip with a larger orifice size. Conversely, if the ratio of fluid to water is greater than desired, the same procedure may be repeated using a smaller orifice size. Still alternatively or in addition to changing the orifice size, the output pressure of the motive source 96 can be adjusted up or down to change the ratio of fluid to water. This process may be repeated until a proper result, such as a desired orifice size, is obtained. Alternatively or in addition to changing the orifice size, the pressure regulator 99 may be adjusted up or down depending on the water concentration. If the water content is too high, the pressure regulator can be regulated down. If the water content is too low, the pressure regulator can be regulated up. Once the regulator is adjusted to a desired set point, the regulator assists in maintaining a constant dilution ratio by maintaining the motive operating pressure at a constant level.

In one exemplary embodiment, a desired motive source pressure is about 17 psi. The metering tip orifice size can be adjusted after fixing the motive source pressure at about 17 psi. Alternatively, once a metering tip is selected, the pressure can be adjusted to produce a desired admixture ratio. In either scenario, once the operating pressure is set, the pressure regulator ensures a constant pressure and a uniform admixture production. Without the pressure regulator, the motive source pressure to the eductor may fluctuate, as is typical of tap water line pressure. However, if an eductor incorporated in a particular system is rated for different operating pressure, then the motive source pressure can vary without deviating from the spirit and scope of the present invention.

Where a motive source line pressure is lower than desired or lower than the eductor recommended operating pressure, a booster pump may be used before the pressure regulator 99. The booster pump can boost up the line pressure and the pressure regulator 99 can be used to regulate the operating pressure to a desired line pressure. If the booster pump incorporates an internal pressure regulator for regulating the maximum pump outlet pressure, then the external pressure regulator 99 may be eliminated.

Although the system 112 shown in FIG. 5 comprises a single inlet suction 46 eductor 20, a two inlet suction eductor 18 (See, e.g., FIG. 1) may also be used to calibrate two orifice sizes simultaneously. When a two inlet suction eductor 18 is used, two metering tips and two tubing hoses are used.

Referring now to FIG. 6, there is shown an alternative proportioning and dispensing system 130 provided in accordance with aspects of the present invention. As shown, a proportioning and dispensing assembly 10 comprising two single suction inlet eductors 20, 21 and one dual suction inlet eductor 18 is used. The system 130 may be used for automatically mixing a plurality of solutions from concentrates, such as a system that produces a disinfectant, a virucide, and a sterilant. In one embodiment, a concentrated disinfectant 132 may be connected, via a tubing 134, to the first eductor 20, a concentrated virucide 136 may be connected to the second eductor 21, and a two-part sterilant comprising a diluent 92 and a concentrated sterilant 94 may be connected to the third eductor 18. In a dental office or in a medical office setting, for example, the system 130 may be incorporated by mounting the proportioning and dispensing assembly 10 on a wall next to a sink and then storing the various chemical containers 92, 94, 132, 136 inside a cabinet 138 below the sink. The cabinet counter-top can be drilled with one or more holes to connect the tubing between the chemical containers 92, 94, 132, 136 located inside the cabinet 138 and the eductors 18, 20, 21 mounted on the wall. One, two, or all three eductors 18, 20, 21 may be operated by activating one, two, or three valves 56 (FIG. 2) at the same time. The various solutions may be blended using metering tip sizes selected in accordance with the methods described hereinabove.

Figure 7:
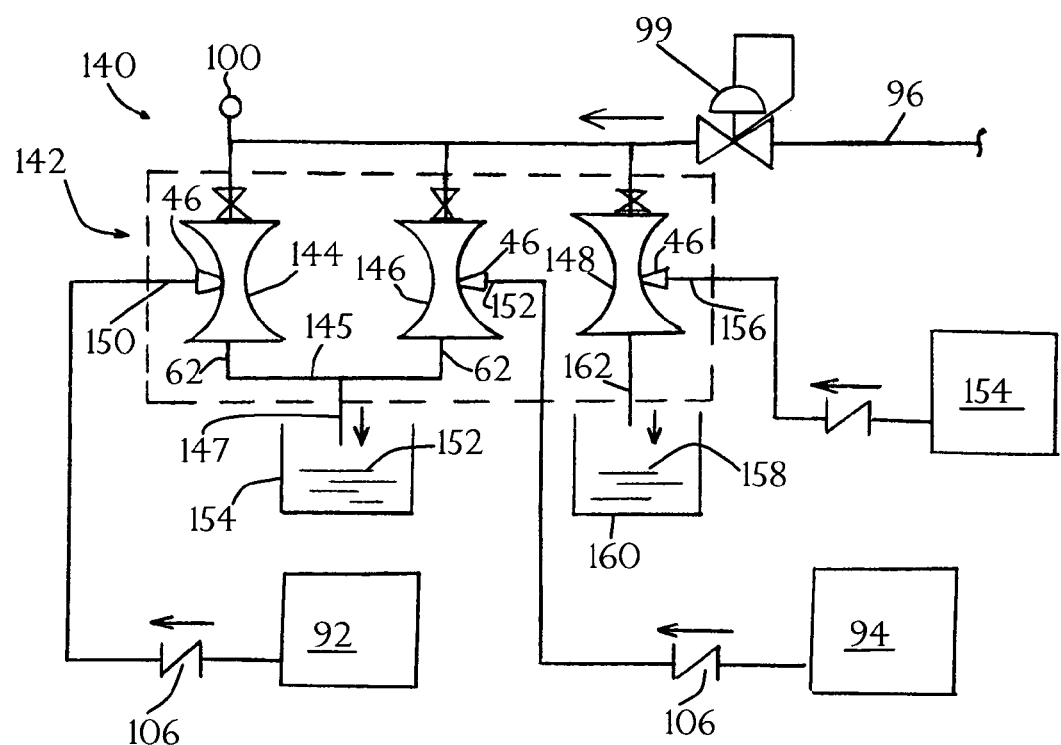
FIG. 7 is an exemplary block flow diagram of a proportioning and dispensing system comprising the proportioning and dispensing assembly of FIG. 1 in service with two of the eductors in parallel service.

Referring now to FIG. 7, there is shown an alternative proportioning and dispensing system 140 provided in accordance with aspects of the present invention. In the system 140 shown, a proportioning and dispensing assembly 142 comprising three single suction inlet eductors 144 are incorporated. Two of the eductors 144, 146 may be used to blend an admixture of a two-part sterilant and the third eductor 148 may be used to blend an admixture of a disinfectant, a sporicide, a biocide, a virucide, or a fungicide.

To implement the system 140 shown in FIG. 7, a container containing diluent 92 is connected to the suction inlet 46 of the first eductor 144 and a container containing a concentrated sterilant 94 is connected to the suction inlet of the second eductor 146. The outlets 62 of the two eductors 144, 146 are connected to a common discharge header 145, which has a single discharge line 147. The metering tip 150 for the first eductor 144 and the metering tip 152 for the second eductor 146 are both selected to provide a desired ratio of admixture 152 in the container 154. In one embodiment, the metering tips 150, 152 are selected in accordance with the procedures described above with reference to FIG. 5.

Depending on the intended use, the third eductor 148 may be connected to a container 154 containing a concentrated disinfectant, a sporicide, a biocide, a virucide, or a fungicide. The metering tip 156 for the third eductor 148 may be selected depending on the desired admixture 158 formed in the holding container 160 at the outlet 162 of the third eductor, and in accordance with the same procedures discussed above.

Although the preferred embodiments of the invention have been described with some specificity, the description and drawings set forth herein are not intended to be delimiting, and persons of ordinary skill in the art will understand that various modifications may be made to the embodiments discussed herein without departing from the scope of the invention, and all such changes and modifications are intended to be encompassed within the appended claims. Various changes to the proportioning and dispensing system including the eductors may be made differently. For example, the eductors can be selected from a different provider, the eductor can be rated for high volume flow, the eductor can be designed for a specific concentrate, the tubing sizes can vary, the mounting location of the fluids and the assembly can be different, and the particular sterilant, disinfectant, antiseptic, sporicide, biocide, virucide, and fungicide can differ. In the embodiments discussed above, the sterilant from Cetylite can also be mixed in the absence of the diluent. Thus, one variation is to eliminate the diluent. Accordingly, many alterations and modifications may be made by those having ordinary skill in the art without deviating from the spirit and scope of the invention.

What is claimed is:

1. A method for dispensing an admixture of fluid and water in a proportioning and dispensing unit comprising the steps:
    (a) selecting a first metering tip comprising a first orifice size and coupling the metering tip to a chemical inlet port of an eductor, said eductor further comprising a water inlet port and an outlet port;

(b) connecting the water inlet port to a water supply source, said water supply source comprising a pressure regulator having a first water pressure set point;

(c) placing a holding container at the outlet port of the eductor for receiving an output stream from the eductor;

(d) selecting a first hose comprising a hose length, a first end, a second end, and unit gradations along at least a portion of the hose length;

(e) placing the first end of the first hose in fluid communication with the metering tip;

(f) filling the hose length with a quantity of fluid to a starting fluid level;

(g) activating the eductor to produce the admixture of fluid and water at the outlet port;

(h) de-activating the eductor to stop producing the admixture at the outlet port;

(i) determining an amount of fluid dispensed from the eductor by measuring the unit gradations on the first hose between the starting fluid level and a second fluid level measured after the eductor is de-activated;

(j) determining a percent ratio of fluid dispensed to water used to dispense the fluid through the eductor; and (k) if the percent ratio of fluid to water is not as desired, changing at least one of the first metering tip having the first orifice size to a second metering tip having a second orifice size and the first water pressure set point of the pressure regulator to a second water pressure set point, and repeating steps (f) to (j).

2. An apparatus for diluting a concentrate comprising:

a proportioning and dispensing unit comprising an eductor, wherein the eductor comprises a chemical inlet port, a motive source inlet port, and an outlet port;

a container containing a concentrate having a container outlet port and a hose connecting the container outlet port to the chemical inlet port;

a line connecting a motive source to the motive source inlet port, the line comprising a pressure regulating valve for regulating pressure supplied by the motive source from a first pressure to a second pressure, which is lower than the first pressure, and a block valve for at least one of opening and blocking the motive source connected in series with the pressure regulating valve;

an outlet hose for connecting to the outlet port of the eductor; and a metering tip removably received in the chemical inlet port.

3. The apparatus of claim 2, wherein the eductor comprises a second chemical inlet port.

* * * * *